US006630663B2

(12) United States Patent
Murphy et al.

(10) Patent No.: US 6,630,663 B2
(45) Date of Patent: *Oct. 7, 2003

(54) MINIATURE ION MOBILITY SPECTROMETER

(75) Inventors: J. Brian Murphy, Culver City, CA (US); Clifford A. Megerle, Thousand Oaks, CA (US); Carl W. Townsend, Los Angeles, CA (US)

(73) Assignee: Raytheon Company, Lexington, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 46 days.

(21) Appl. No.: 09/176,561

(22) Filed: Oct. 21, 1998

(65) Prior Publication Data

US 2003/0155503 A1 Aug. 21, 2003

(51) Int. Cl.[7] ................................................. H01J 49/40
(52) U.S. Cl. ....................................... 250/286; 250/287
(58) Field of Search ................................ 250/286, 287, 250/281, 282

(56) References Cited

U.S. PATENT DOCUMENTS

| 4,271,357 A | * | 6/1981 | Bradshaw et al. ........... 250/287 |
| 4,831,254 A | * | 5/1989 | Jenkins ........................ 250/286 |
| 5,047,723 A | | 9/1991 | Puumalainen |
| 5,083,019 A | * | 1/1992 | Spangler ...................... 250/286 |
| 5,184,015 A | * | 2/1993 | Allman et al. ............... 250/286 |
| 5,455,417 A | * | 10/1995 | Sacristan ...................... 250/287 |
| 5,723,861 A | * | 3/1998 | Carnahan et al. ............ 250/287 |
| 5,789,745 A | * | 8/1998 | Martin et al. ................. 250/286 |
| 5,811,059 A | * | 9/1998 | Genovese et al. ............ 250/287 |
| 5,965,882 A | * | 10/1999 | Megerle et al. .............. 250/287 |
| 6,255,648 B1 | * | 7/2001 | Littlejohn et al. ............ 250/286 |

OTHER PUBLICATIONS

"M90 Chemical Warfare Agent Detection System", Environics OY, Mikkeli, Finland No page and No dated.

* cited by examiner

Primary Examiner—Kiet T. Nguyen
(74) Attorney, Agent, or Firm—Colin M. Raufer; Leonard A. Alkov; Glenn H. Lenzen, Jr.

(57) ABSTRACT

An ion mobility spectrometer includes a housing with a flow channel, an air pump to force air through the flow channel, a heater at an inlet end of the flow channel, and an ionization source that ionizes the air after it is heated. The heated, ionized air passes through an electric field produced by a field source and a plurality of sensor elements located within in the wall of the flow channel in the measurement region of the electric field. The sensor elements include a plurality of sensor electrodes in one wall of the flow channel. Ion currents to the sensor electrodes are measured by an integrated high-sensitivity readout circuit array, permitting the sensor electrodes to be quite small. The sensor electrodes may be arranged in one-dimensional or two-dimensional arrays.

21 Claims, 4 Drawing Sheets

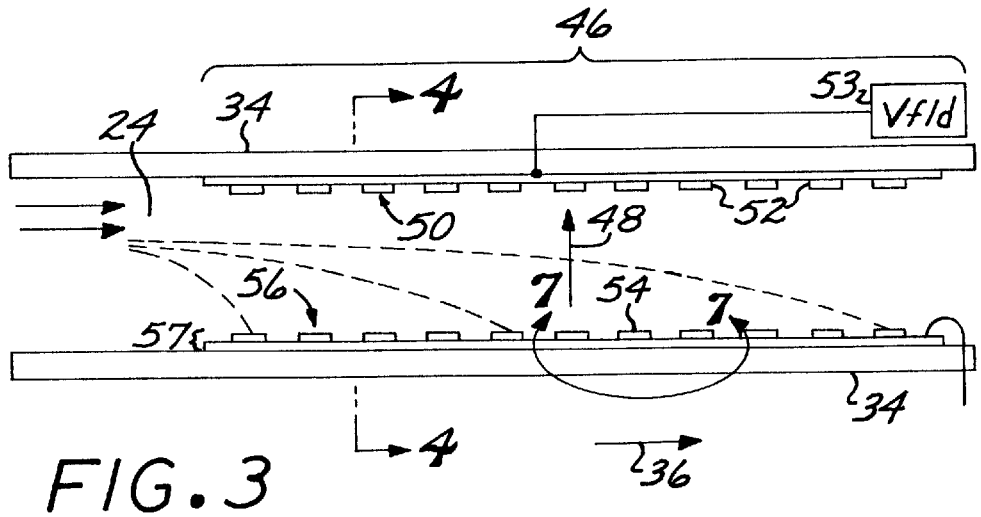
FIG. 3
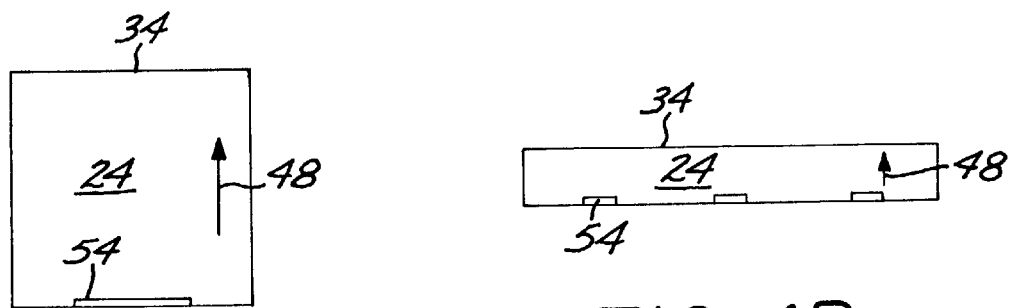
FIG. 4A
FIG. 4B
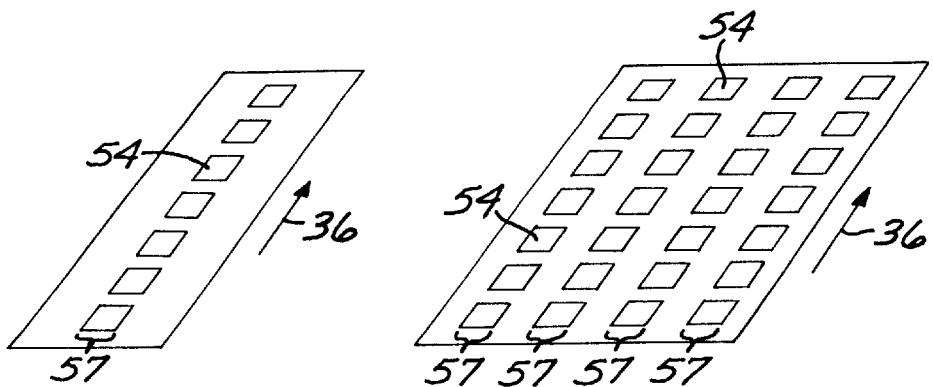
FIG. 5
FIG. 6

MINIATURE ION MOBILITY SPECTROMETER

BACKGROUND OF THE INVENTION

This invention relates to the measurement and identification of species in a flowing gas sample, and, more particularly, to a miniature device for performing such determinations.

A person may be exposed to small amounts of species, such as organic agents, that may be quite harmful to the person's health. For example, a soldier may be exposed to chemical warfare agents, a chemical worker may be exposed to leakages or spills, or a rescue worker may enter a situation where unknown chemical agents, some of which may be harmful, may be present. In each such situation, it is important to know whether any such species are present and, if so, the nature of the species so that the person may take the necessary precautions.

Where the concentrations of the species are relatively large, they may often be detected by the senses of the person, such as a characteristic smell, or a physiological reaction of the person, such as watering eyes. However, many species either cause no such reactions, or cause harm even when present in concentrations below the human detection level. A measurement device is required for determining the presence of these very low concentrations, and such a device may be necessary even if the person detects or has a reaction to the species, in order to identify the exact species.

In a known type of ion mobility spectrometer used to determine the presence of species, a sample of air or other gas, usually heated, is ionized and passed through a flow channel. A transverse electric field deflects the ionized species. The amount of deflection depends upon several factors, including, for example, the size of the ion and its electrical charge, the air flow rate, and, secondarily, the mass of the molecule. Electrodes positioned in the wall of the flow channel collect the ions, and the ion current flow at each electrode is a measure of the number of ions reaching that electrode. From the distribution of the electrode currents and pre-established calibration information, information regarding the nature of the species may be deduced.

Existing M-90 ion mobility spectrometers, which may operate from a battery, are rather large in size, about 11 inches by 11 inches by 4 inches, and heavy, about 15 pounds (including battery pack), and are thus too large to be considered a "personal" instrument to be carried in the pocket. The M-90 instrument has only two sets (channels) of three electrodes each, limiting the possible chemical resolution of the instrument. Large air flow rates (up to 2 liters per minute) are used, requiring large power consumption to heat the air and force it through the flow channel. The M-90 ion mobility spectrometer has a relatively high power consumption, requiring a large, bulky battery pack when used in the self-contained mode.

To be considered a "personal"-sized ion mobility spectrometer for at least some applications and as used herein, an ion mobility spectrometer must have a total volume of less than about 40 cubic inches, a weight of less than about 2 pounds (including battery pack), and an operating life of at least about 12 hours from a portable battery power source without recharging or replacing the battery. The existing devices cannot meet this requirement. Other types of gas flow analysis devices that meet these requirements do not have the operating advantages of the ion mobility spectrometer.

Thus, there is a need for a miniature, personal-sized ion mobility spectrometer. The present invention fulfills this need, and further provides related advantages.

SUMMARY OF THE INVENTION

The present invention provides the first miniature, personal-sized ion mobility spectrometer for the identification of chemical species in a gas sample. A preferred form of the ion mobility spectrometer of the invention has approximate dimensions of 6 inches by 3 inches by 2 inches and weighs less than 2 pounds.

The ion mobility spectrometer of the invention is more sensitive and has higher selectivity than prior devices operating according to the principle of ion mobility spectrometry. Due to the higher sensitivity of its physical structure and the electronics, the ion mobility spectrometer of the invention may operate using lower air flow rates and has a longer operating life on a smaller single set of batteries prior to recharging or replacement. The ion mobility spectrometer may therefore be readily carried in a hand or a pocket of the user. It may be powered by a conventional battery pack commonly used for personal-sized, hand-held instruments, such as a BA5800/U battery pack issued by the US Government. Additionally, the analysis of chemical species is more precise than possible with existing ion mobility spectrometer devices, because larger numbers of sensing elements and two-dimensional arrays of sensing elements may be incorporated.

In accordance with the invention, an ion mobility spectrometer comprises a spectrometer cell having a gas inlet, a gas outlet, and a flow channel therebetween. The flow channel has a wall, a gas inlet end at the gas inlet, and a gas outlet end at the gas outlet. A downstream direction, the direction of air flow, is defined from the gas inlet to the gas outlet, and an opposite upstream direction is defined from the gas outlet to the gas inlet.

A field source of an electric field, including opposed, facing pairs of electrodes positioned at the facing walls of the flow channel, establishes an electric field over a measurement region of the flow channel. The electric field is perpendicular to the local direction of air flow. The sensor electrodes on one side of the flow channel, which form a part of the sensor elements, are preferably at or near ground potential. The opposing field electrodes that are paired with these sensor electrodes are connected to a power supply to provide them with an electrical potential. In this way, electric fields are established between pairs of electrodes in the measurement region. Equivalently, the multiple field electrodes may be provided as a single field electrode extending over the entire measurement region.

For most applications, at any moment in time all of the electric fields are preferably of the same polarity and oriented in the same direction, providing a nearly uniform field through which the ions migrate. However, other approaches may be desirable in other circumstances. For example, the electric fields may be of mixed polarity, such as with the leading electrodes first encountered by the gas flow of one polarity and the remaining electrodes of opposite polarity. In another example, it may be desirable to have a nonuniform field strength, such as with a lower voltage field produced by the leading electrodes and a higher voltage field produced by the remaining electrodes.

A plurality of sensor elements utilize the plurality of respective sensor electrodes (those which are at or near ground potential), and an electrically communicating readout circuit array integral with or attached to the plurality of sensor electrodes. The readout circuit detects and amplifies the ion current reaching each of the sensor electrodes. The readout circuit array comprises an integrated circuit operable to detect an electrical charge accumulation or ion current on each of the sensor electrodes. An important feature of this invention is the use of monolithic pre-amplification circuitry. This readout device contains one preamplification circuit for each sensor electrode or channel. The preamplification circuits are optimized for low noise and amplification of low currents.

The ion mobility spectrometer further includes an air pump operable to force gas through the flow channel, a gas heater in the flow channel upstream of the source of the electric field and the plurality of sensor elements in the measurement region, and an ionization source in the flow channel upstream of the source of the electric field and the plurality of sensor elements.

The personal-sized ion mobility spectrometer has a size of less than about 40 cubic inches and a weight of less than about 2 pounds (including the battery), and is operable on battery power for at least 12 hours before replacement or recharging of the battery. The readout circuit electronics of the ion mobility spectrometer is sensitive to ion currents of less than about 1 picoampere.

In operation of the ion mobility spectrometer, a gas such as air is drawn into the gas flow channel and heated to a preselected constant temperature. The heated gas is passed through an ionizing region, so that any organic or other species to be detected are ionized. The gas, possibly containing such ionized species, is passed through the electric field, which causes the ionized species to be angularly deflected according to the sense and magnitude of the electric field. The amount of deflection also depends upon the size, charge, mass, and other properties of the species, as well as the flow rate of the gas. In general, though, larger species are deflected less than smaller species, so that the smaller species contact the sensor electrodes on the wall of the gas flow channel upstream of the larger species. As the ions strike the sensor electrodes in the wall, their charge is transferred to the sensor electrodes and an electrical current flows in the preamplification readout circuit. The ratios of the current flows at the various sensor electrodes forms a pattern that reveals the type of ionized species in the air. The magnitude of these current flows is related to the concentration of these species in the flowing air. From this information and calibration data obtained using known amounts of known species, the single or multiple species in the flowing sample may be determined. See, for example, U.S. Pat. No. 5,047,723, whose disclosure is incorporated by reference. The calibration information is preferably stored in look-up tables in a memory of the ion mobility spectrometer, so that identification of unknown species may be made as the data is gathered.

The polarity of the electrodes may be fixed. In another embodiment, the polarity of the electrodes may be periodically changed so as to force ions of positive charge to the sensor electrodes during a first period of time, and later to force ions of negative charge to the same sensor electrodes during a second period of time. In this case, the positively and negatively charged ions would be detected alternately by the one set of sensor electrodes.

The sensor electrode array may be separate from the readout chip, or may be an integral part of it. The use of an integrated electrode and readout circuit allows the sensor electrodes to be made much smaller than previously possible in devices of this type. The use of smaller sensor electrodes leads to much higher spatial resolution of the mass distribution. Different types of sensor electrode arrays may be used, so that multiple types of data may be gathered. Additionally, the smaller sensor electrodes allow the gas flow rate to be reduced, reducing the amount of air that must be drawn through the gas flow channel and heated, and therefore the power requirements of the device. This, in turn, allows the gas flow channel to be smaller in cross section than previously possible. The use of the smaller sensor electrodes also allows the use of a two-dimensional array of sensor electrodes within the gas flow channel without enlarging the size of the cell. A two-dimensional array of sensor electrodes may be used to gather more information about the ionized species in the gas flow than can a one-dimensional array.

Accordingly, the miniaturization of the sensor elements is advantageous both in improving the portability of the ion mobility spectrometer and achieving a personal-sized device, and also in improving its data-gathering ability. Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

BRIEF DESCRIPTION OF THE DRAWINGS

FIGS. 1A–1B are perspective views of ion mobility spectrometers according to the invention, wherein FIG. 1A illustrates a rectangular housing and FIG. 1B illustrates a curved, coiled housing FIGS. 2A–2B are schematic sectional views of the ion mobility spectrometer of FIG. 1A, taken along lines 2—2, wherein FIG. 2A is a straight, linear version, and FIG. 2B is a folded version;

FIG. 3 is an enlarged detail of FIG. 2A, showing the measurement region;

FIGS. 4A and 4B are cross sectional views of the gas flow channel as it passes through the measurement region, taken along line 4—4 of FIG. 3, wherein FIG. 4A illustrates a first embodiment and FIG. 4B illustrates a second embodiment;

FIG. 5 is a perspective view of a one-dimensional sensor element array;

FIG. 6 is a perspective view of a two-dimensional sensor element array;

DETAILED DESCRIPTION OF THE INVENTION

Figure 1A:
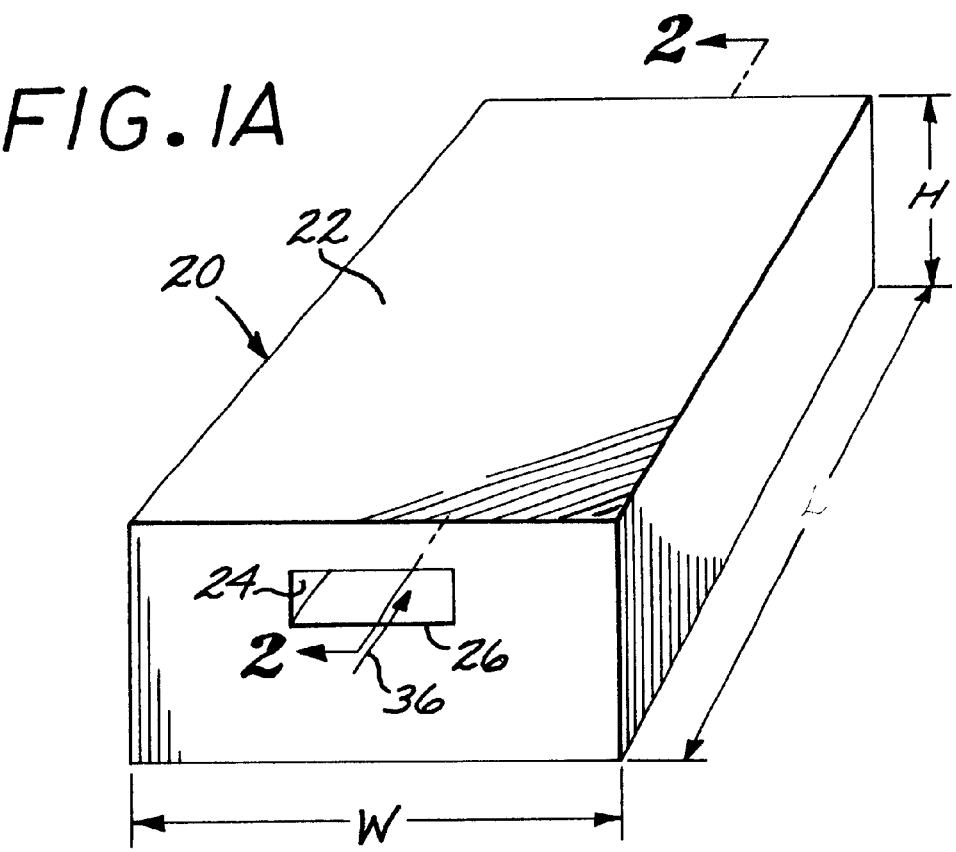

FIG. 1A is a perspective schematic view of an ion mobility spectrometer 20 according to the present invention. The ion mobility spectrometer 20 includes a housing 22 having a gas flow channel 24 therethrough. In the view of FIG. 1A, a gas flow inlet 26 of the gas flow channel 24 may be seen. The overall dimensions of the ion mobility spectrometer 20 are a width W of about 3 inches, length L of about 6 inches, and a height H of about 2 inches. The ion mobility spectrometer 20 of FIG. 1 weighs about 2 pounds, including its battery power source.

The small size of the ion mobility spectrometer 20 is conducive to its use in other, less conventional shapes. FIG.

1B illustrates the ion mobility spectrometer 20 having a flexible housing 22 wrapped around its battery.

Figure 1B:
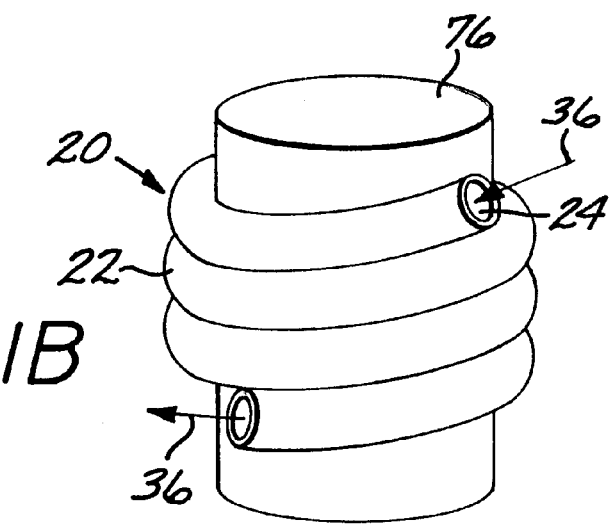
Figure 2A:
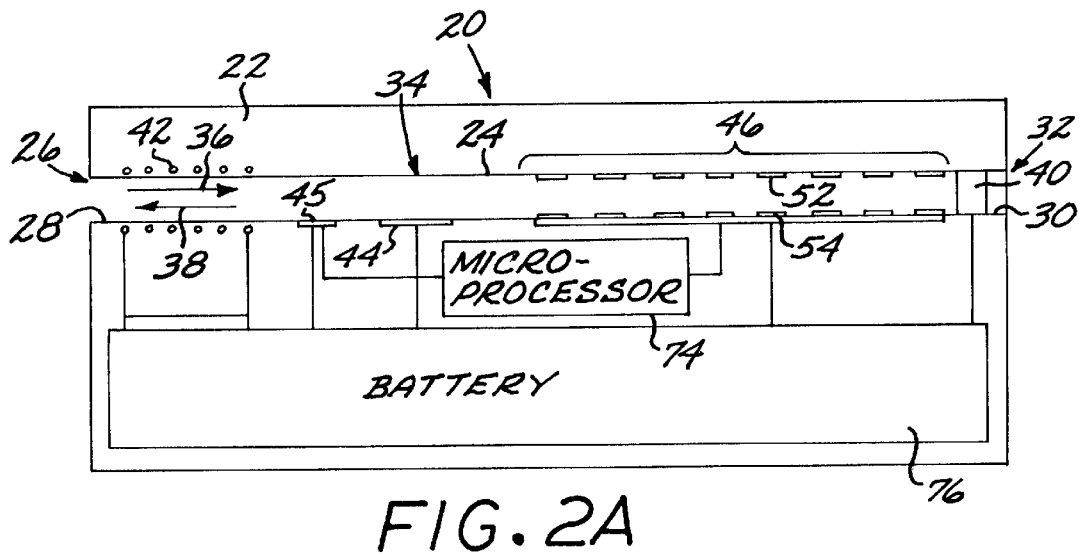
Figure 2B:
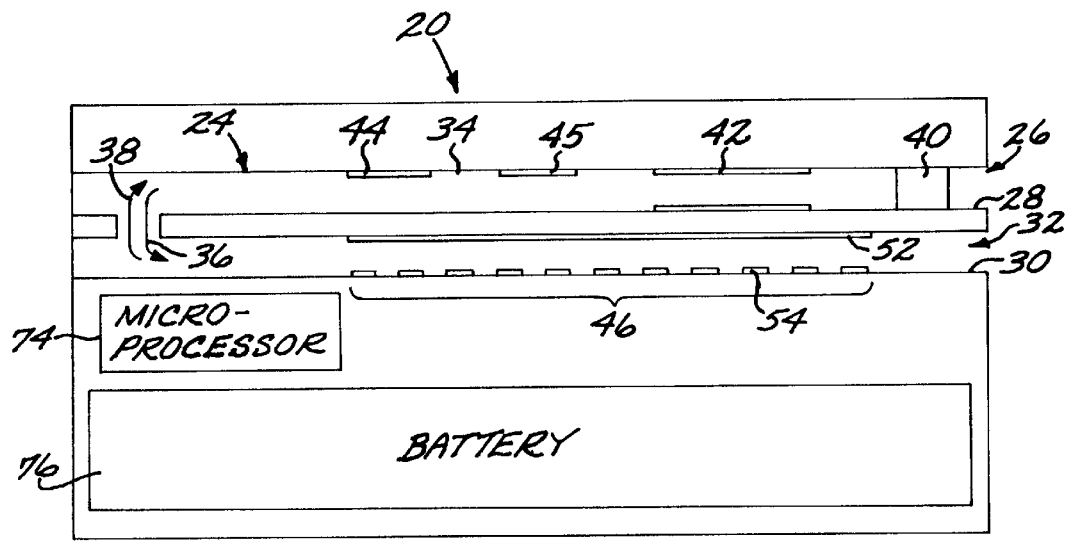

FIGS. 2A–2B schematically illustrates the interior structure of the ion mobility spectrometer 20. FIG. 2A shows the ion mobility spectrometer 20 in a form having a straight, linear gas flow channel 24. FIG. 2B shows the ion mobility spectrometer 20 in a form having a gas flow channel 24 that is "folded" to conserve space. In each case, the gas flow channel 24 has an inlet end 28 at the gas flow inlet 26 and an outlet end 30 at a gas flow outlet 32, and a wall 34 extending therebetween. A downstream direction 36 along and through the gas flow channel 24 is defined as the direction from the inlet end 28 to the outlet end 30 of the gas flow channel 24. An upstream direction 38 is opposite to the downstream direction 34, from the outlet end 30 to the inlet end 28. The downstream and upstream directions are measured along the gas flow channel, and they are therefore straight (FIG. 2A), folded (FIG. 2B), or curved (FIG. 1B) with the flow channel 24, as appropriate.

An air pump 40 is positioned to draw air into the inlet end 28 of the gas flow channel 24 and force it through the gas flow channel 24 in the downstream direction 34 toward the outlet end 30. The air pump 40 may be near the outlet end 20 as pictured in FIG. 2A, the inlet end 28 as pictured in FIG. 2B, or at an intermediate location. The drawn-in air may contain small amounts of chemical species that are to be detected if present. The drawn-in air is heated by a heater 42 of any operable type, positioned at the wall 34 of the gas flow channel 24 to a preselected constant temperature such as about 35° C. FIG. 2A illustrates a heater 42 in the form of a coil of wire wound around the gas flow channel, and FIG. 2B illustrates a flat-plate heater. The heating to constant temperature negates the effects of temperature variability of molecular mobility and density, which would otherwise interfere with the measurements. The heated air is passed across an ionization source 44 located in the wall 34 of the gas flow channel 24. The ionization source 44 may be of any operable type, but is preferably a radioactive source such as a small amount of Americium ($^{241}$Am), which ionization source requires no power consumption. The species of interest, if present in the air, are ionized by the ionization source 44.

Properties of the air flow such as its temperature, flow rate, and humidity are measured by conventional instrumentation 45, which may be located at any operable location along the gas flow channel 24.

The flow of air, possibly having ionized species therein, enters a measurement region 46 of the gas flow channel 24, which is shown in greater detail in FIG. 3. In the measurement region 46, the gas flow channel 24 is preferably rectangular in cross section, as shown in FIGS. 4A and 4B. The cross section of the gas flow channel 24 may be either square or nearly square, as shown in FIG. 4A, or an elongated rectangle as shown in FIG. 4B.

An electric field, indicated by arrow 48 is applied to the interior of the gas flow channel 24 over the length of the measurement region 46 by a source 50 of an electric field. The electric field 48 extends transversely to the gas flow. That is, the electric field 48 is locally perpendicular to the downstream direction 36 and extends between opposing walls 34. The source 50 of the electric field is conveniently a plurality of counterelectrodes 52 in one wall 34, with a voltage $V_{fld}$ applied to each counterelectrode 52 by a power supply 53 relative to a facing sensor electrode 54 in the opposing wall. This embodiment allows different voltages to be applied to different ones of the counterelectrodes 52. Equivalently for many purposes where the same field voltage is to be applied through the entire measurement region, a single counterelectrode 52 may be used, extending over the length of the measurement region 46 as shown in FIG. 2B. The applied voltage $V_{fld}$ and thence the electric field may be constant, may be controllably varied over time, and/or may be reversed over time, so as to gather information in a wide variety of electric field types and magnitudes.

A plurality of sensor elements 56 are provided. Each sensor element 56 utilizes the sensor electrode 54 as its sensing element. The number of sensor elements 56 and sensor electrodes 54 is preferably more than three and most preferably more than five, to gather the most useful data for construction of histograms. The sensor electrodes 54 are arranged in a group 57 extending parallel to the downstream direction 36. As used herein, a "group" of sensor electrodes are those sensor electrodes over which a single streamline of gas passes when flowing in the downstream direction 36, and which are used to build a single histogram of information. FIG. 3 illustrates eleven sensor electrodes 54 in the singe group. FIGS. 4A and 5 show a single group of sensor electrodes 54 in a linear, one-dimensional array. Additional sensor electrodes 54 may be added in parallel groups to form a two-dimensional array of sensor electrodes 54, as shown in FIGS. 4B and 6. The two-dimensional array of sensor electrodes offers the potential for improved performance by using different electric fields for each group, for example.

As noted above, for a single group of sensor electrodes, the applied voltage $V_{fld}$ and thence the electric field may be controllably varied and/or reversed over time, in order to obtain additional information. Much the same effects may be obtained simultaneously with a two-dimensional sensor electrode array by biasing different groups of counterelectrodes 52 differently. In this case, rows between the biased groups are held at ground potential to separate from each other regions in the sensor cell that have different electric fields.

As the ionized species in the gas flow pass through the measurement region 46, they are deflected toward the direction perpendicular to the downstream direction 36, so as to strike the sensor electrodes 54. The sensor elements 56 collect and amplify the ion currents resulting from the charge accumulation on their respective sensor electrodes 54 due to the impacting of the ionized species. The plurality of sensor elements 56 allow histograms to be developed that may be linked to the specific types of species in the gas flow. (The data analysis does not form a part of the present invention.)

Figure 7:
FIG. 7 is a further enlarged detail of FIG. 3, taken in region 7—7, showing the integrated readout circuits and electrodes.

Each sensor element 56 includes the sensor electrode 54 positioned at one wall 34 of the gas flow channel 24. The electrical charge collected at each sensor electrode 54 over a period of time is periodically measured by a readout device 60, or "readout". The readout 60 is preferably a monolithic integrated circuit having the required circuitry deposited in multiple layers 62, as shown in FIG. 7. The sensor electrode 54 may be fabricated separately from the readout 60 and bonded to an upper surface 64 of the readout 60, or it may be deposited integrally as a metallization on the upper surface 64 as the last step in the production of the integrated circuit readout. A passivation layer 65, such as a layer of $SiO_2$, may be applied between the sensor electrodes 54 to reduce surface leakage between the sensor electrodes 54.

Figure 8:
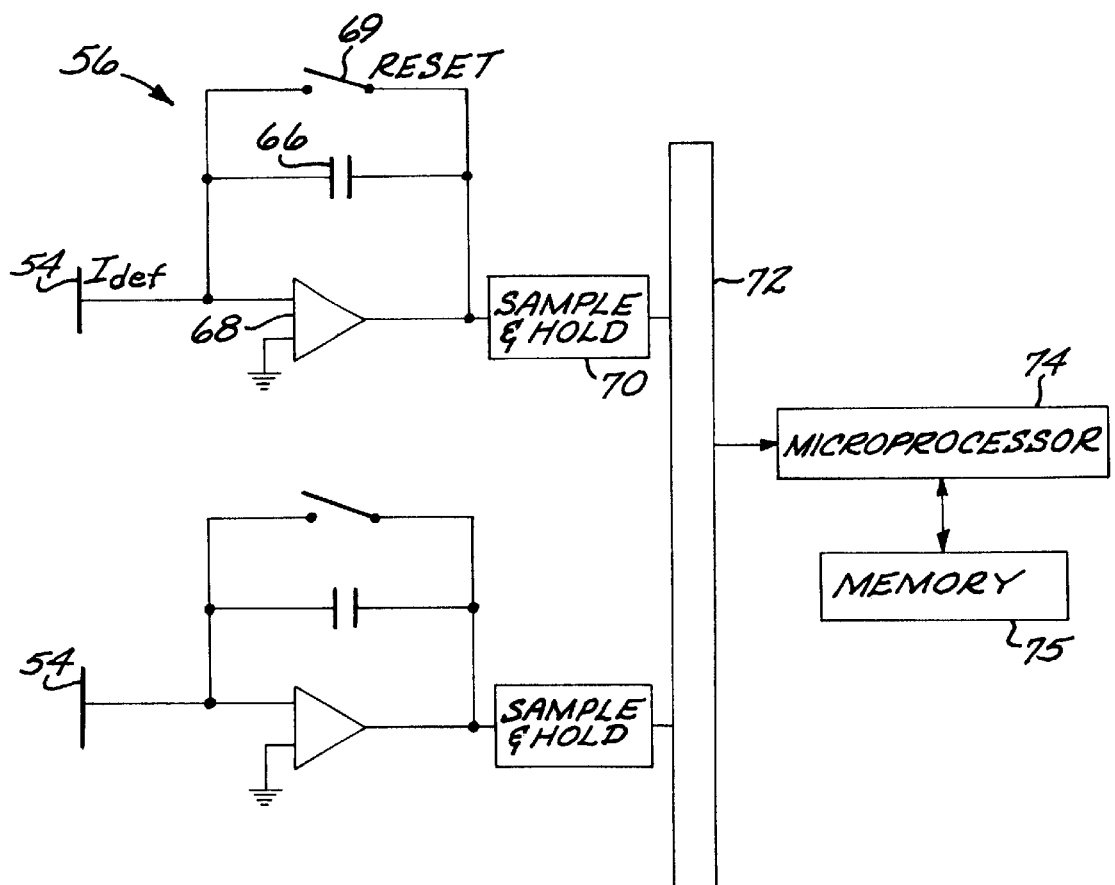
FIG. 8 is a circuit diagram of a preferred readout circuit array.

FIG. 8 illustrates a preferred circuitry for the readout 60, for two of the sensor electrodes 54. The readout preferably includes an array of capacitive feedback transimpedance amplifiers. The electrical charge carried to the electrode 54 by the deflected ion species is collected on a feedback capacitor 66. The resulting current is amplified by an amplifier 68. The amplified current is sampled by a sample-and-hold circuit 70. The data from the plurality of sensor elements 56 are periodically strobed to a multiplexer 72 and provided to a data analysis microprocessor 74 having an associated memory 75. The feedback capacitor 66 is shorted by a reset 69 to prepare it for the next data collection period.

Any operable sampling procedure may be used in reading the output of the amplifier 68. Preferably, a double-correlated sampling approach is employed. The sample-and-hold device captures the output voltage of the amplifier 68 just after each reset ($V_1$) and just before the next reset ($V_2$). The difference in these voltages is used in a double-correlated sampling scheme which tends to cancel noise in the voltage sampling, according to $$V_2 - V_1 = I(t/C)$$

where I is the current, t is the integration time, and C is the capacitance of the capacitor 66. With a 0.1 picofarad capacitor and a 10 millisecond integration period, the transimpedance is about $10^{11}$ volts per ampere. The integration time may be varied, either generally or on a sensor element-by-sensor element basis, to alter the sensitivity of the measurement. Data values may be signal averaged over a period of time to further negate the effects of noise.

Based upon the scaling of the air flow, battery size, air heating requirements, and other scalable quantities, it is estimated that the amplifier must be operable to sense currents of less than about 1 picoampere, and preferably less than about 500 femtoamperes, in order to allow reduction of the size and weight of the ion mobility spectrometer so as to be classified as a "personal" instrument, while meeting the operating life requirements without a recharge or replacement of the battery power supply. If the amplifier cannot sense such small currents, the volume of air that must flow through the ion mobility spectrometer is so large as to prevent scaling down to sizes and weights into the "personal" range discussed previously.

The sensor electrodes 54 are each preferably, but not necessarily, of about 1 to about 5 square millimeters in size. This electrode area is about ⅕ of that of the existing M90 ion mobility spectrometer, which has a current detection capability of about 5 picoamperes. Thus, any miniature ion mobility spectrometer with a current detection capability of less than about 1 picoampere will yield an improved performance over that of the existing instrument, in a "personal"-sized device. The present approach allows currents of 4 femtoamperes or smaller to be reliably measured, less than ¹⁄₁₀₀₀ that possible with the approach used in the prior battery-powered ion mobility spectrometer.

The microprocessor 74 and memory 75 are contained within the housing 22. The components of the ion mobility spectrometer, including the air pump 40, the heater 42, the electrical field source 50, the readout 60, and the microprocessor 74, all may be powered from an external source. However, one objective of the miniaturization of the invention is to provide a portable unit. The preferred system therefore includes a battery power supply 76 within or attached to the housing. In the embodiment of FIG. 1B, the curved housing 22 is wrapped around the battery power supply 76 to conserve volume. (Not all of connections to the microprocessor 74 and to the battery power supply 76 are shown, to achieve clarity in the drawings. These connections will be apparent to those skilled in the art.)

In prior approaches to ion mobility spectrometers, the charges collected from the deflected ionized species were sensed as the voltage drop across a large resistor. The greatest sensitivity practically possible with this approach is approximately 5 picoamperes. This sensitivity limit imposed a limit on the number of sensor elements that could practically be used, because the current for each sensor element is related to the total concentration of ionized species divided by the number of sensor elements. If too many sensor elements were used in the prior approach, the available current would be too low and the device unusable.

The inventors' recognition of the criticality of the amplification capability and the use of the monolithic integrated circuit approach results in surprising and unexpected benefits. First, the number of sensor elements may be increased significantly, either as more sensor elements in the one-dimensional array of FIG. 5 or as additional groups of sensor elements in the two-dimensional array of FIG. 6. In the prior approach, the maximum number of sensor elements was three in each of two groups or channels. Increasing the number of sensor elements in a group improves the sensitivity and resolution of the information gathered, because there are more points in the histogram distribution. Data may also be gathered in smaller time increments. Second, the ion mobility spectrometer may be made much smaller in size and weight that previously possible. The smallest prior portable ion mobility spectrometer is about 11 inches by 11 inches by 4 inches in size, weighing about 15 pounds. This prior unit may be carried about, but is not a "personal"-sized device, as defined previously, that may be carried on the person of the user such as in a pocket. A presently preferred embodiment of the ion mobility spectrometer of the present invention is about 6 inches by 3 inches by 2 inches in size, weighing about 2 pounds. It also is readily adapted to many other applications of interest such as air-dropped pods.

The reduction in size and weight of the measuring instrumentation allows all of the supporting components to be correspondingly reduced in size and weight. A smaller gas flow channel allows the use of a smaller air pump 40 and a smaller heater 42, reducing the required capacity and size of the battery 76. For example, the existing M-90 ion mobility spectrometer cannot be operated for 12 hours from the standard BA5800/U battery pack, which supplies 42 watt-hours of power, and which is used by the US military to power hand-carried global positioning system receivers. The preferred embodiment of the present ion mobility spectrometer uses less than 2 watts of power, and specifically about 1.7 watts of power, well below the 3.5 watts limit to operate a device using a BA5800/U power supply for a required 12 hour mission.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. An ion mobility spectrometer, comprising:
   a spectrometer cell having
      a gas inlet,
      a gas outlet, and
      a flow channel therebetween, the flow channel having a wall, a gas inlet end at the gas inlet, and a gas outlet end at the gas outlet, there being a downstream direction from the gas inlet to the gas outlet and an upstream direction from the gas outlet to the gas inlet;
   a field source of an electric field in the wall of the flow channel extending over a measurement region of the flow channel, the electric field extending perpendicular to the downstream direction;

a plurality of sensor elements in the wall of the flow channel along the measurement region, the plurality of sensor elements including
- a plurality of sensor electrodes arranged in a two-dimensional array on a first side of the flow channel, and
- a readout circuit array integral with the plurality of sensor electrodes wherein the readout circuit array contains a preamplification circuit for each of the plurality of sensor electrodes, the readout circuit array comprising an integrated circuit operable to detect an electrical charge accumulation on each of the sensor electrodes, wherein each of the plurality of sensor electrodes arranged in a two-dimensional array may be subject to a non-uniform electric field polarity and a non-uniform electric field voltage;

an air pump operable to force gas through the flow channel;

a gas heater in the flow channel upstream of the source of the electric field and the plurality of sensor elements;

an ionization source in the flow channel upstream of the source of the electric field and the plurality of sensor elements; and a housing enclosing the spectrometer cell, the field source, the plurality of sensor elements, the air pump, the gas heater, and the ionization source.

2. An ion mobility spectrometer, comprising:

a spectrometer cell having
- a gas inlet,
- a gas outlet, and
- a flow channel extending between the gas inlet and the gas outlet, the flow channel having a wall, a gas inlet end at the gas inlet, and a gas outlet end at the gas outlet, there being a downstream direction from the gas inlet to the gas outlet and an upstream direction from the gas outlet to the gas inlet;

a field source of an electric field in the wall of the flow channel extending over a measurement region of the flow channel, the electric field extending perpendicular to the downstream direction;

a plurality of sensor elements in the wall of the flow channel along the measurement region, the plurality of sensor elements including
- a plurality of sensor electrodes on a first side of the flow channel, and
- a readout circuit array integral with the plurality of sensor electrodes, the readout circuit array comprising an integrated circuit operable to detect an electrical charge accumulation on each of the sensor electrodes;

an air pump operable to force gas through the flow channel;

a gas heater in the flow channel upstream of the source of the electric field and the plurality of sensor elements;

an ionization source in the flow channel upstream of the source of the electric field and the plurality of sensor elements;

a battery operably connected to power the spectrometer cell, the air pump, and the gas heater; and a housing enclosing the spectrometer cell, the field source, the plurality of sensor elements, the air pump, the gas heater, and the ionization source.

3. The ion mobility spectrometer of claim 2, wherein the plurality of sensor elements comprises a chip having deposited thereon multiple layers, the multiple layers including an intergrated readout circuit array, and an electrode layer having the plurality of sensor electrodes patterned thereon.

4. The ion mobility spectrometer of claim 2, wherein the readout circuit array comprises at least one capacitive feedback transimpedance amplifier.

5. The ion mobility spectrometer of claim 2, wherein the readout circuit array comprises a plurality of capacitive feedback transimpedance amplifiers.

6. The ion mobility spectrometer of claim 2, wherein the plurality of sensor electrodes comprises a one-dimensional array of sensor electrodes.

7. The ion mobility spectrometer of claim 2, wherein the plurality of sensor electrodes comprises a two-dimensional array of sensor electrodes.

8. The ion mobility spectrometer of claim 2, wherein the readout circuit array is operable to sense currents of less than about 1 picoampere.

9. The ion mobility spectrometer of claim 2, wherein the ion mobility spectrometer has a volume of less than about 40 cubic inches and a weight of less than about 2 pounds.

10. The ion mobility spectrometer of claim 2, wherein the gas heater is upstream of the ionization source.

11. The ion mobility spectrometer of claim 2, wherein the ion mobility spectrometer is sized so as to be portable to be carried on the person of a user.

12. An ion mobility spectrometer, comprising:

a spectrometer cell having
- a gas inlet,
- a gas outlet, and
- a flow channel extending between the gas inlet and the gas outlet, the flow channel having a wall, a gas inlet end at the gas inlet, and a gas outlet end at the gas outlet, there being a downstream direction from the gas inlet to the gas outlet and an upstream direction from the gas outlet to the gas inlet;

a field source of an electric field in the wall of the flow channel extending over a measurement region of the flow channel, the electric field extending perpendicular to the downstream direction;

a plurality of sensor elements in the wall of the flow channel along the measurement region, the plurality of sensor elements including
- a plurality of sensor electrodes on a first side of the flow channel, and
- a readout circuit array operable to sense currents of less than about 1 picoampere, wherein the readout circuit array is integral with the plurality of sensor electrodes, and the readout circuit array comprises an integrated circuit operable to detect an electrical charge accumulation on each of the sensor electrodes;

an air pump operable to force gas through the flow channel;

a gas heater in the flow channel upstream of the source of the electric field and the plurality of sensor elements;

an ionization source in the flow channel upstream of the source of the electric field and the plurality of sensor elements;

a battery operably connected to power the spectrometer cell, the air pump, and the gas heater for at least about 12 hours without recharging or replacing the battery; and a housing enclosing the spectrometer cell, the field source, the plurality of sensor elements, the air pump, the gas heater, the ionization source, and the battery, wherein the ion mobility spectrometer has a volume of less than about 40 cubic inches and a weight of less than about 2 pounds, and wherein the ion mobility spectrometer is portable and may be carried on the person of a user.

13. The ion mobility spectrometer of claim 12, wherein each of the sensor electrodes has an area of from about 1 square millimeter to about 5 square millimeters.

14. An ion mobility spectrometer, comprising:
   a spectrometer cell having
      a gas inlet,
      a gas outlet, and
      a flow channel extending between the gas inlet and the gas outlet, the flow channel having a wall, a gas inlet end at the gas inlet, and a gas outlet end at the gas outlet, there being a downstream direction from the gas inlet to the gas outlet and an upstream direction from the gas outlet to the gas inlet;
   a field source of an electric field in the wall of the flow channel extending over a measurement region of the flow channel, the electric field extending perpendicular to the downstream direction;
   a plurality of sensor elements in the wall of the flow channel along the measurement region, the plurality of sensor elements including
      a plurality of sensor electrodes on a first side of the flow channel, and
      a readout circuit array;
   an air pump operable to force gas through the flow channel;
   a gas heater in the flow channel upstream of the source of the electric field and the plurality of sensor elements;
   an ionization source in the flow channel upstream of the source of the electric field and the plurality of sensor elements; and
   a battery operably connected to power the spectrometer cell, the air pump, and the gas heater for at least about 12 hours without recharging or replacing the battery, wherein the ion mobility spectrometer has a volume of less than about 40 cubic inches and a weight of less than about 2 pounds, and wherein the ion mobility spectrometer is portable and may be carried on the person of a user.

15. The ion mobility spectrometer of claim 14, wherein the plurality of sensor elements comprises a chip having deposited thereon multiple layers, the multiple layers including
   an integrated readout circuit array, and
   an electrode layer having the plurality of sensor electrodes patterned thereon.

16. The ion mobility spectrometer of claim 14, wherein the readout circuit array comprises
   at least one capacitive feedback transimpedance amplifier.

17. The ion mobility spectrometer of claim 14, wherein the plurality of sensor electrodes comprises a one-dimensional array of sensor electrodes.

18. The ion mobility spectrometer of claim 14, wherein the plurality of sensor electrodes comprises a two-dimensional array of sensor electrodes.

19. The ion mobility spectrometer of claim 14, wherein the readout circuit array is operable to sense currents of less than about 1 picoampere.

20. The ion mobility spectrometer of claim 14, further including
   a housing enclosing the spectrometer cell, the field source, the plurality of sensor elements, the air pump, the gas heater, the ionization source, and the battery.

21. The ion mobility spectrometer of claim 14, wherein the readout circuit array is integral with the plurality of sensor electrodes.

* * * * *